(12) United States Patent
Herron

(10) Patent No.: US 9,272,114 B2
(45) Date of Patent: Mar. 1, 2016

(54) HEATED CPAP HOSE AND FITTING

(75) Inventor: Roy Herron, Starr, SC (US)

(73) Assignee: Flexible Technologies, Inc., Abbeville, SC (US)

( * ) Notice: Subject to any disclaimer, the term of this patent is extended or adjusted under 35 U.S.C. 154(b) by 503 days.

(21) Appl. No.: 13/525,709

(22) Filed: Jun. 18, 2012

(65) Prior Publication Data

US 2013/0333701 A1  Dec. 19, 2013

(51) Int. Cl.
*A61M 16/00* (2006.01)
*A61M 16/08* (2006.01)
*H05B 3/58* (2006.01)
*A61M 16/10* (2006.01)
*A61M 16/16* (2006.01)

(52) U.S. Cl.
CPC ....... *A61M 16/0875* (2013.01); *A61M 16/1075* (2013.01); *A61M 16/1095* (2014.02); *A61M 16/16* (2013.01); *H05B 3/58* (2013.01); *A61M 2205/3368* (2013.01)

(58) Field of Classification Search
CPC ............ A61M 16/00; A61M 16/0003; A61M 16/0057; A61M 16/106; A61M 16/08; A61M 16/0808; A61M 16/0875; A61M 16/1045; A61M 16/1075; A61M 16/1085; A61M 16/1095; A61M 39/00; A61M 39/10; A61M 39/12; A61M 2039/10; A61M 2039/1022; A61M 2039/1027; A61M 2205/3368; A61M 2205/36
USPC ........................... 138/33, 104, 132, 122, 109; 439/578–585; 128/202.27, 204.17, 128/204.18, 204.21, 205.25, 206.21, 912; 285/903
See application file for complete search history.

(56) References Cited

U.S. PATENT DOCUMENTS

| | | | |
|---|---|---|---|
| 4,447,707 A | 5/1984 | Baker | |
| 4,553,023 A | 11/1985 | Jameson | |
| 4,667,084 A | 5/1987 | Regge | |
| 4,725,713 A | 2/1988 | Lehrke | |
| 5,859,953 A | 1/1999 | Nickless | |
| 5,974,227 A | 10/1999 | Schave | |
| 6,953,354 B2 * | 10/2005 | Edirisuriya et al. | 439/191 |
| 7,263,984 B2 | 9/2007 | Wade et al. | |
| 7,383,745 B2 | 6/2008 | Eiteneer et al. | |
| 8,028,721 B2 | 10/2011 | Koskey | |
| 8,726,901 B2 * | 5/2014 | Jassell et al. | 128/200.24 |
| 2008/0105257 A1 * | 5/2008 | Klasek et al. | 128/203.27 |
| 2009/0223514 A1 * | 9/2009 | Smith et al. | 128/203.14 |
| 2011/0244724 A1 * | 10/2011 | Whitlock et al. | 439/580 |
| 2012/0125333 A1 * | 5/2012 | Bedford et al. | 128/203.25 |
| 2013/0112201 A1 * | 5/2013 | Graham et al. | 128/203.27 |
| 2014/0202460 A1 * | 7/2014 | Bath et al. | 128/202.22 |

* cited by examiner

*Primary Examiner* — Justine Yu
*Assistant Examiner* — Douglas Sul
(74) *Attorney, Agent, or Firm* — Thomas A. O'Rourke; Bodner & O'Rourke, LLP

(57) ABSTRACT

A flexible hose is adapted to maintain its inner wall temperature above the dew point of air transported between a CPAP machine's humidifier and mask, preventing condensation. An electrically energizable heating element forms a helical reinforcement member. The hose's first end has a standard CPAP soft end cuff. The second end comprises a special end fitting including: a support ring, electrical jack, and a specially shaped over-molded plastic cuff. The support ring has a ring portion threadably secured onto the helical reinforcing member, and a receptacle extending therefrom. A coaxial electrical jack is received within the receptacle, with the energizable heating element of the helix being wired to the prongs of the jack. A soft plastic cuff is molded over much of the ring portion and receptacle, to provide further integrity of the end fitting, while the remaining portion of the cuff conforms to the standard CPAP end cuff configuration.

17 Claims, 14 Drawing Sheets

(1 + 1 Wire Arrangement)
( Least Heat)

(1 + 2 Wire Arrangement)

(2 + 2 Wire Arrangement)

(2 + 3 Wire Arrangement)
(Most Heat)

HEATED CPAP HOSE AND FITTING

FIELD OF THE INVENTION

The present invention relates to improvements in flexible heated hoses, and more particularly to improvements to such hoses to more efficiently accommodate a power connection to supply power to a heating element of the hose.

BACKGROUND OF THE INVENTION

There are many applications in which a hose is used to transport material-gases, liquids, particulates, a slurry, etc., and the material to be transported requires its temperature to remain elevated for one or more different reasons. Therefore, heated hoses being adapted for particular applications are known within the art.

For example, U.S. Pat. No. 4,553,023 to Jameson is for "Thermally Insulated Electrically Heated Hose for Transporting Hot Liquids." The Jameson hose is specifically adapted for transporting molten adhesive from a melter to a dispenser, and comprises a Teflon tube having two hard plastic cuffs at the ends, each of which have a hard plastic tube extending radially from a side thereof for accommodating the exit of the electrical leads.

Another example is shown by U.S. Pat. No. 8,028,721 to Koskey for a "Heated Garden Hose For Cold Weather Use." The Koskey heated hose includes a standard garden hose that is secured onto one leg of a Y-coupler, with the second end of the Y-coupler being used for receiving an inlet coupler for hooking the hose to a faucet spout. An electrical heating cable is mated to the branch of the "Y" with its plug being exposed therefrom, and with the cable portion free-floating within the standard garden hose portion to heat water as it flows therein.

Both of these prior art heated hoses loosely exemplify the two main construction types utilized for the heating of materials within tubes and hoses. The first utilizes a rigid fitting to support the electrical termination, but this construction type is in direct opposition to the use of a soft plastic cuff, which is preferable to many end users, especially for a continuous positive airway pressure (CPAP) machine, because a soft cuff provides a more positive connection and is identical to the current, proven, attachment design for standard non-heated CPAP hoses.

The second utilizes a molded plastic end "cuff" or fitting from which a flexible cord extends to accommodate the electrical wires and a plug/receptacle in an umbilical arrangement, to relieve stresses imposed upon the electrical connection with the fitting. However, this construction type, in addition to being aesthetically less attractive, has several significant drawbacks: it results in a higher per/unit cost due to the extra cord and plug that are required; it results in a heavier hose arrangement due to the extra weight of that cord and plug; and it affects long term reliability, as the extra plug and cord constitute one more connection that can fail. Where just a soft end cuff is used without the umbilical arrangement, failure results quickly as the soft cuff material does not have the strength to retain the electrical connection throughout repeated cycles of insertion/removal of the power connector, and it is ultimately dislodged or ripped loose exposing live wiring inside the cuff.

The heated hose of the current invention includes a cuff that uniquely accommodates the electrical connection to overcome the drawbacks of the prior art, while permitting the desirability of the soft cuff interface.

OBJECTS OF THE INVENTION

It is an object of the invention to provide a flexible hose that is usable for transporting air between a CPAP humidifier and mask.

It is another object of the invention to provide a flexible hose that may accommodate an electrically energizable heating element to heat the inner hose wall and prevent condensation from forming therein.

It is a further object of the invention to provide a flexible hose that may utilize soft over-molded end cuffs that provide a durable electrical connection therein and a positive fluid connection with the CPAP mask and humidifier.

Further objects and advantages of the invention will become apparent from the following description and claims, and from the accompanying drawings.

SUMMARY OF THE INVENTION

The flexible heated wire hose of the current invention is particularly adapted to warm the hose wall to keep its temperature above the dew point of the moisture-laden air transported between a CPAP humidifier and a mask, to prevent condensation from forming therein, which may secondarily serve to warm the air. The flexible heated wire hose may comprise: a hose portion having a first end and a second end; a first end fitting; and a second end fitting. The hose may comprise a reinforcement member being formed generally into a series of flexible turns with each turn being spaced from an adjacent one of the turns to create an interstitial area, with the turns being covered by one or more layers of a flexible material, preferably being a thermoplastic elastomer (TPE).

One of the end fittings may be used for coupling of the heated hose to a CPAP mask, and may therefore comprise a standard 22 mm CPAP soft cuff in the form of plastic molded over the second end of the hose. The plastic may be the same as is used for the hose covering, and preferably is a TPE. The other end fitting may be used for attaching the hose to the outlet vent of a CPAP humidifier and is specifically constructed to receive a coaxial power connector of a power supply to accomplish the heating therein. This end fitting may comprise: a support ring, a coaxial electrical jack, and plastic that forms a standard soft "cuff" portion that may be received by the humidifier, where the plastic may be adhered to the hose, the support ring, and the coaxial electrical jack using one of several different approaches. The plastic may be directly molded over selective features of both the support ring and the jack, and over a portion of the hose, to integrate and encapsulate them within a single integral end fitting. Alternatively, the plastic may be adhered to the first end of said hose by the plastic cuff being molded separately and thereafter being applied onto the first end of the hose over the support ring and jack, with the plastic cuff being adhered thereto using either or both adhesive and/or mechanical fasteners, which includes, but is not limited to, a bolt and a nut being used to secure a seam in the soft plastic.

The coaxial electrical jack may be fixedly received within a receptacle of the support ring, which is in turn fixed to the hose. The support ring may be fixed to the hose using either or both of an adhesive layer and/or internal threading on the inside surface of the ring that is threadably received by at least a portion of one turn of the series of turns of the reinforcing member.

Heating of the hose wall may be provided by the reinforcing member comprising an electrically energizable heating element that is electrically coupled to the jack to receive power therefrom, where a pair of prongs extending from the jack may conveniently accommodate such electrical coupling. The heating element may preferably comprise a first wire and a second wire being electrically coupled to the first prong of the jack, and a third wire being insulated from the first and second wires and being electrically coupled to the second prong of the jack, where the first and second wires and the third wire are each formed into the series of flexible turns to serve as the reinforcing member for the flexible cover. The first and second wires are electrically coupled to the third wire, in proximity to the end of the hose having the standard 22 mm CPAP soft cuff end fitting.

To conveniently accommodate receiving of the coaxial power connector of a power supply within the electrical jack, the receptacle of the support ring, and thus the electrical jack, may be oriented at a 45 degree angle to the axis of the ring portion of the support ring that is to be secured upon the one or more turns of the hose.

DETAILED DESCRIPTION OF THE INVENTION

Figure 1:
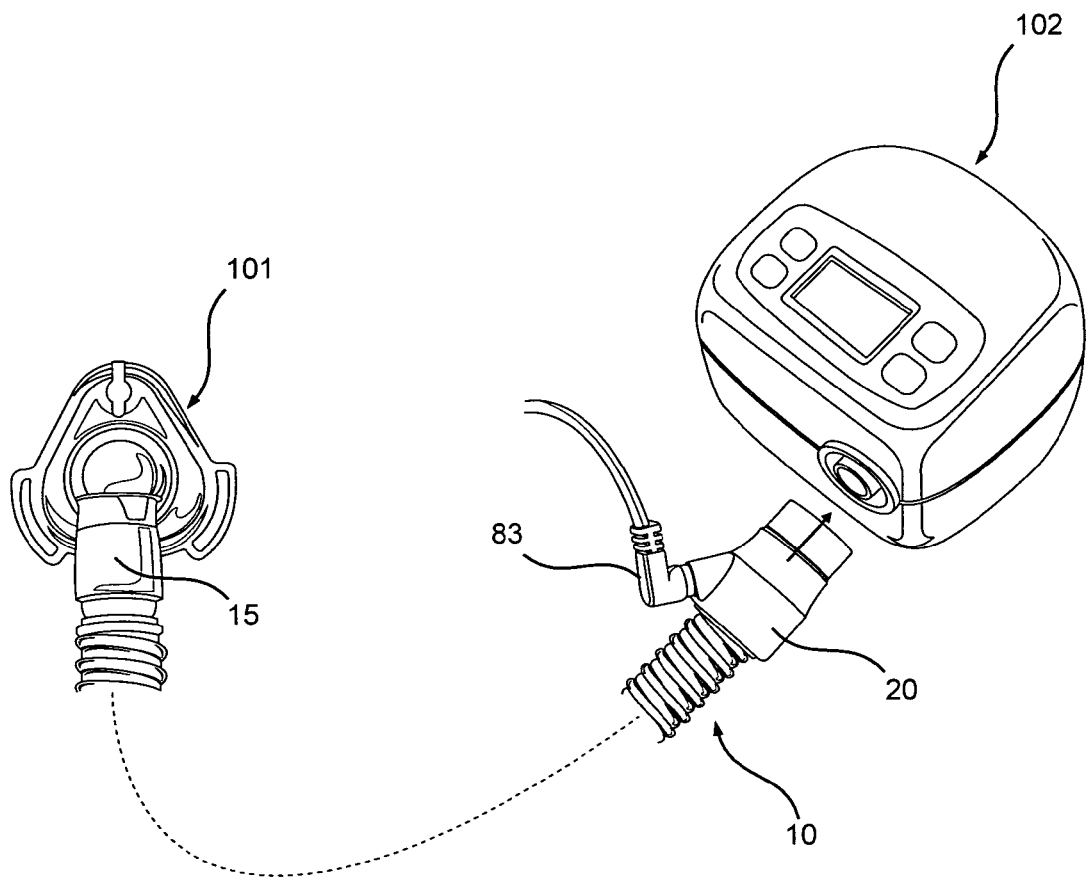
FIG. 1 is a perspective view showing the fitting of the heated hose of the current invention being inserted into the outlet vent of a CPAP humidifier, with the opposite end having a standard soft over-molded CPAP cuff already connected to the inlet valve of a mask.
Figure 2A:
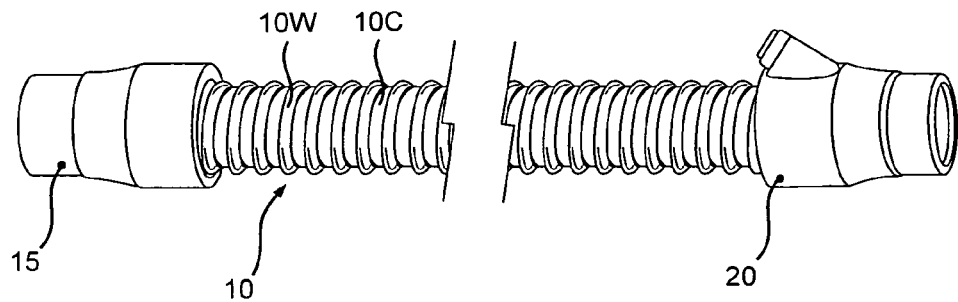
FIG. 2A is a perspective view of a heated hose with a standard CPAP-connectable end cuff on one end fitting of the hose, and the CPAP-connectable end fitting according to the present invention on the other end of the tube.
Figure 3:
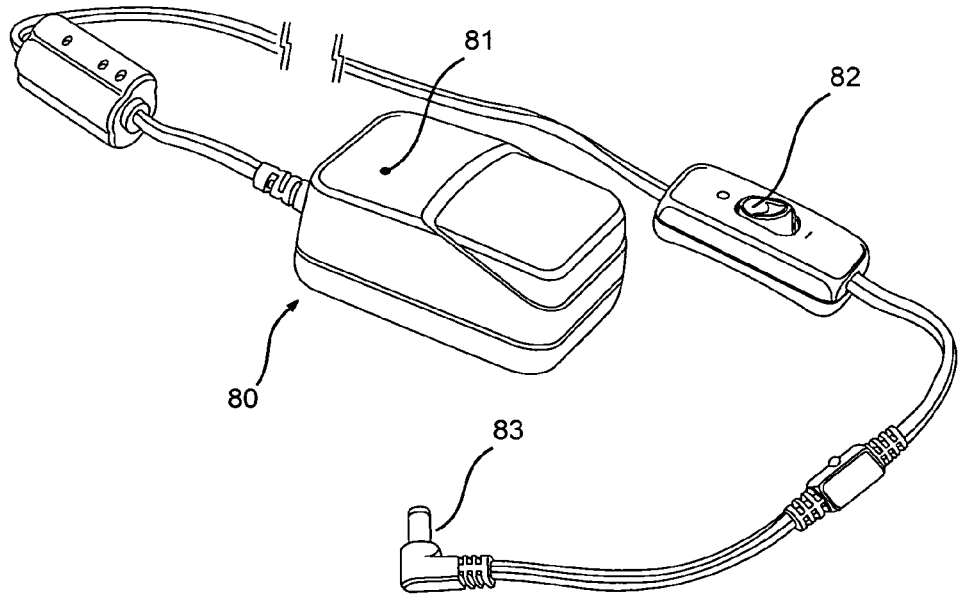
FIG. 3 is a perspective view of the power supply components of the present invention for independently powering the heating element of the hose of the present invention.

FIG. 1 shows a heated hose 10 of the current invention, which comprises a first end fitting 15 that has been coupled with the inlet valve of a CPAP mask 101 to be in fluid communication therewith, and comprising a second end fitting 20 just prior to being coupled with an outlet vent of a CPAP humidifier 102. The hose 10 is shown by itself in FIG. 2A, while the hose's independent power supply apparatus 80 is shown in FIG. 3.

The construction of the hose 10 may comprise a wire reinforcing member 10W, which may be wound through a series of turns to preferably produce a flexible shape similar to that of a helical spring. The turns of the reinforcing member 10W, as well as the interstitial space between the turns, may receive one or more plies of material to create a flexible cover 10C, having a suitably sized inner diameter to conduct the flow of air. The plies of material of the flexible cover may preferably be a thermoplastic elastomer (TPE), which is commonly used for CPAP hoses. The plies may be formed so as to have an inward or outward fold between the turns while the hose 10 is in the undeflected condition. Merely to be exemplary, in an embodiment where the CPAP hose is constructed to have a standard six foot length, the inner diameter of the tube may be sized to be 19 mm, and may thereby serve to provide a flow resistance of less than 1.0 cm of H2O (0.1 kPa) at 60 SLP.

Figure 2B:
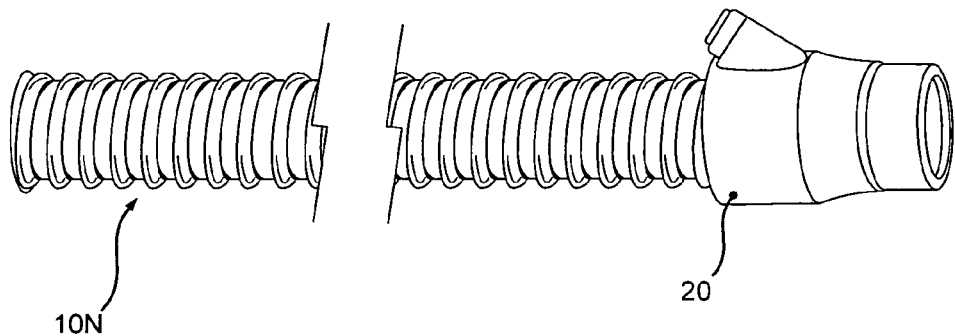
FIG. 2B is a perspective view of a heated hose with the CPAP-connectable fitting according to the present invention on one end of the tube, and the other end being without a molded end cuff.

A first end of the hose for attachment to the CPAP mask need not have an end fitting formed thereon, as seen for hose 10N in FIG. 2B, because the first end of the hose may be secured to the mask using a hose clamp, including, but not limited to, the clamp disclosed within U.S. Pat. No. 5,115,541 to Stichel, the disclosures of which are incorporated herein by reference. However, a more easily releasable and quicker means of securing the first end of the hose to the mask may be desired, and therefore the first end may more preferably have molded thereon, a standard 22 mm CPAP soft cuff 15, which is known in the art. The over-molded soft cuff 15 may preferably be formed using the same material as was used for forming the hose, for compatibility—in order for it to bond with the hose portion, and therefore, it may preferably be a thermoplastic elastomer.

Figure 9:
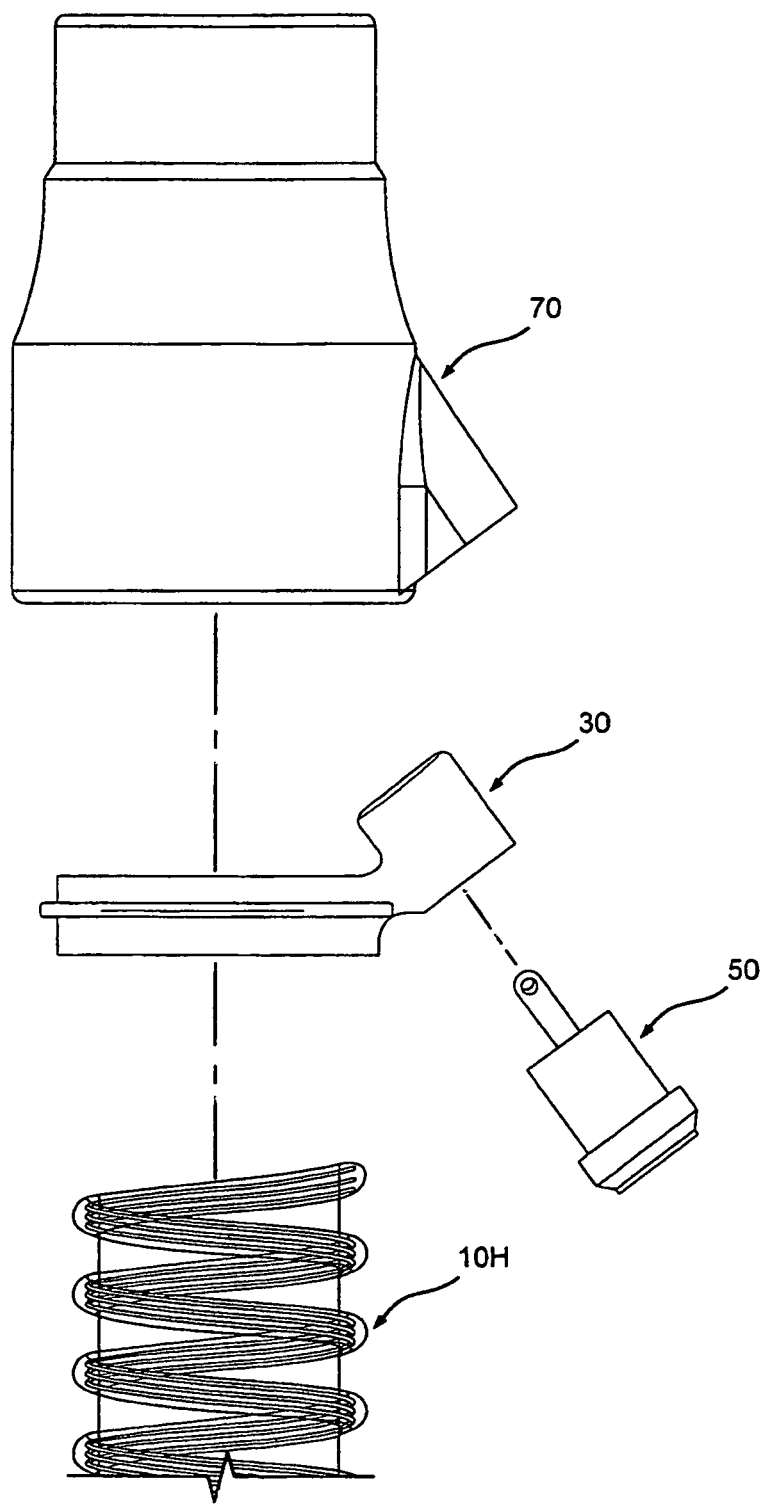
FIG. 9 is an exploded view of the parts comprising the first end of the heated hose of FIG. 5.

The second end of the hose, as seen for both hose 10 in FIG. 2A and hose 10N in FIG. 2B, may have an end fitting 20 according to the present invention. End fitting 20 is shown enlarged within the views of FIGS. 5-8. The end fitting 20 may be formed of several components, which are illustrated within the exploded view of FIG. 9, and may include: a specially configured support ring 30, an electrical jack 50, and plastic 70 that seals and integrates the ring, the jack, and the hose, and also forms a standard soft "cuff."

The support ring 30 (FIGS. 10-11B) must generally not be made of a conductive material, and must be formed of a material that provides sufficient rigidity. The support ring 30 may therefore be made of polyethylene (PA); polypropylene; polyamide (PA); polyester (linear ester plastics); polyethylene (PE) such as polyethylene terephthalate (PET); Polyvinylchloride (PVC); polyvinylidene chloride (PVDC); or cellulose acetate (CA). If a conductive material such as aluminum were to be used for support ring 30, it would need to be coated with an insulating material. The support ring may comprise a hollow cylindrical member 33 having a first generally planar end 31 and a second generally planar end 32, and an outer cylindrical surface 33T and an inner cylindrical surface 33I. Protruding outward from the outer cylindrical surface 33T may be an annular protrusion 34 that spans from a first planar end 34A to a second planar end 34B, and has an outer surface 34T.

Support ring 30 may also comprise a cylindrical receptacle 40 having: a generally planar first end 41 and a generally planar second end 42; an outer cylindrical surface 40T and an inner cylindrical surface 40I; and an end wall 43 extending from the planar end surface 42 toward the first planar surface to form the cylindrical receptacle. The end wall 43 may have two openings, 44, and 45, which may be rectangular openings therein. Protruding outward from the outer cylindrical surface 40T may be an annular protrusion 46 that spans from a first planar end 46A to a second planar end 46B, and has an outer surface 46T.

The cylindrical receptacle 40 may be formed separately and thereafter be joined/attached to the cylindrical member 33 using any suitable means, including, but not limited to, adhesive bonding, welding, etc. Alternatively, the cylindrical receptacle 40 may be integrally formed with the support ring 30 to form a better structural connection therebetween. The cylindrical receptacle 40 may be formed with the support ring 30 so as to have its axis 40X be roughly oriented at a 45 degree angle with the axis 31X of cylinder 33, the significance of which will become apparent within a later discussion. In addition, the open end of the receptacle may preferably be disposed on the side of the receptacle that faces away from the axis 31X of the cylinder 31.

Figure 10:
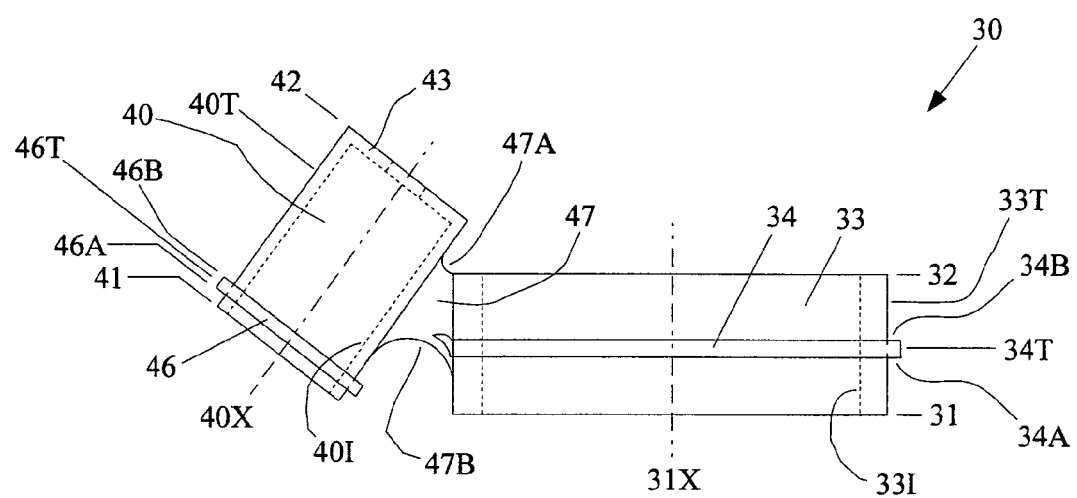
FIG. 10 is a side view of the support ring of FIG. 5.
Figure 11A:
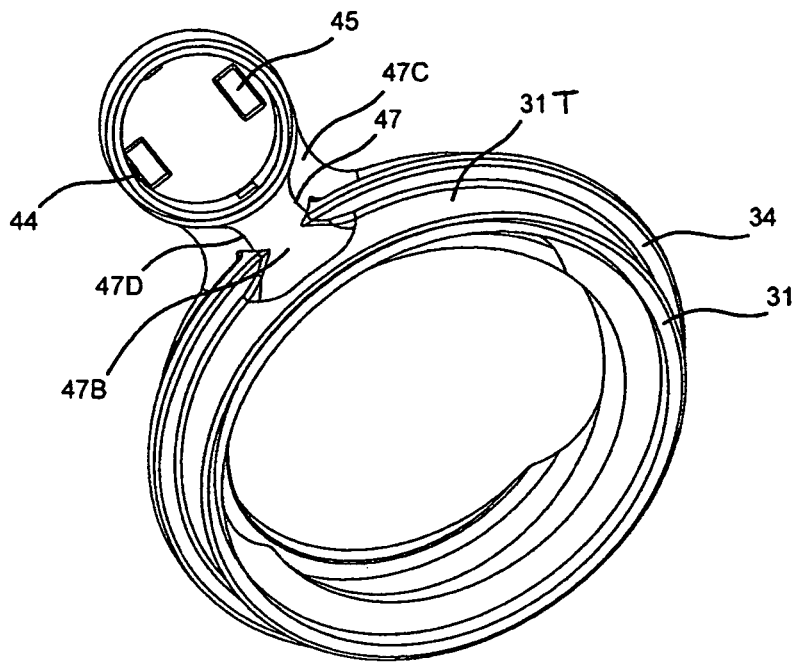
FIG. 11A is a bottom perspective view of the support ring of FIG. 5.
Figure 11B:
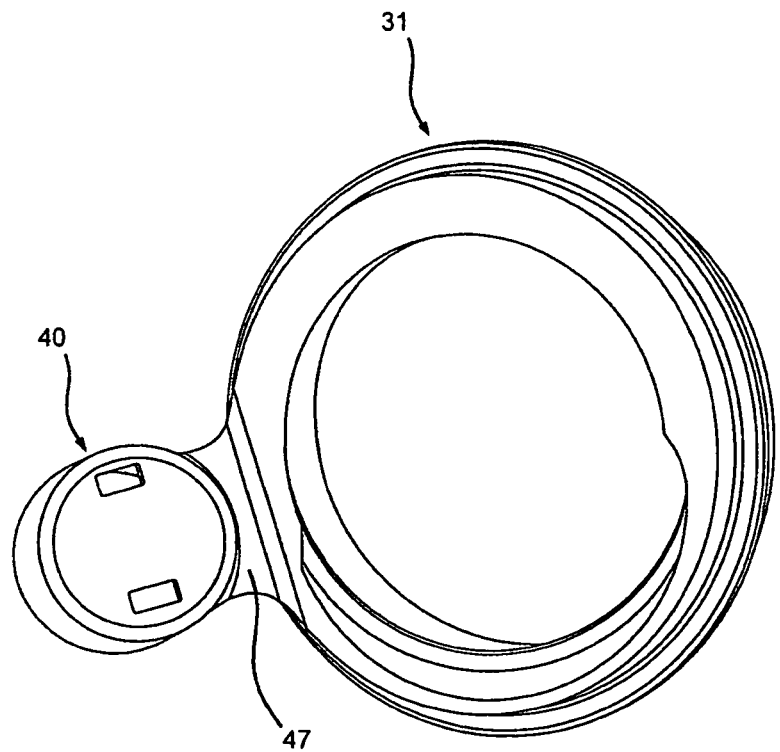
FIG. 11B is a top perspective view of the support ring of FIG. 12.

As seen in FIG. 10, a neck 47 may be integrally formed with the cylindrical receptacle 40 and the cylindrical member 33 using a suitably generous fillet radius 47A that may be tangent to both the second generally planar end 32 of the cylinder 33 and the side of the receptacle 40 in the direction of the receptacle axis 40X, and using a suitably generous fillet radius 47B that may be tangent to both the outer cylindrical surface 33T of the cylinder 33 in the direction of the cylinder axis 31X and the side of the receptacle 40 in the direction of the receptacle axis 40X. The neck 47 may also comprise fillets 47C and 47D (FIG. 11A). Fillet 47B, as seen in FIG. 11A, may locally subsume the extent of the annular ring 34.

Figure 18:
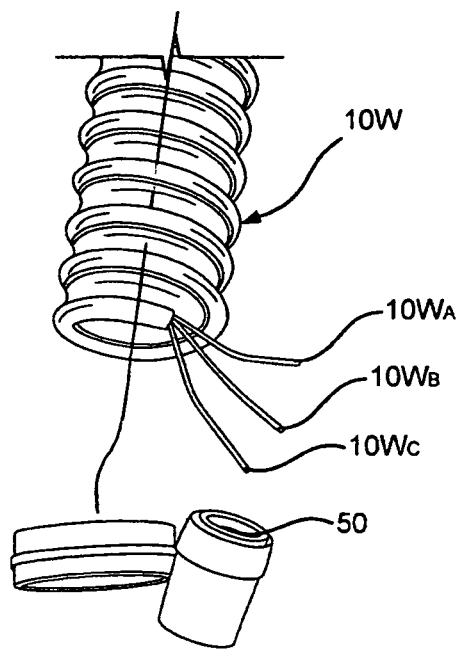
FIG. 18 is a perspective view showing the joined support ring and coaxial electrical jack of FIG. 14, just prior to being secured to the flexible hose.
Figure 19:
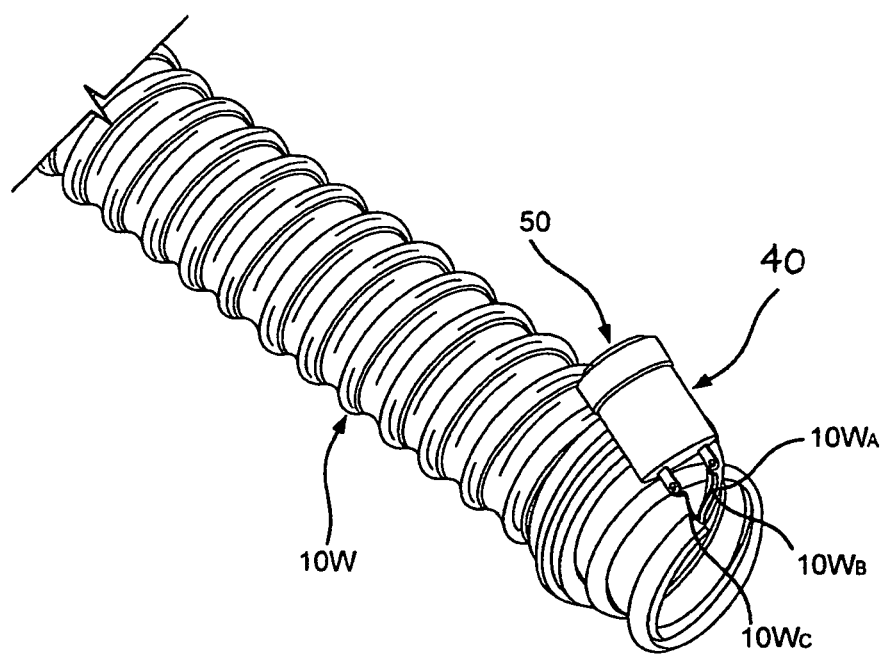
FIG. 19 is a perspective view showing the joined support ring and coaxial electrical jack of FIG. 14, just after being secured to the flexible hose, and with the electrical wires comprising the hose's helical reinforcing member having been secured to the prongs of the coaxial electrical jack.
Figure 20:
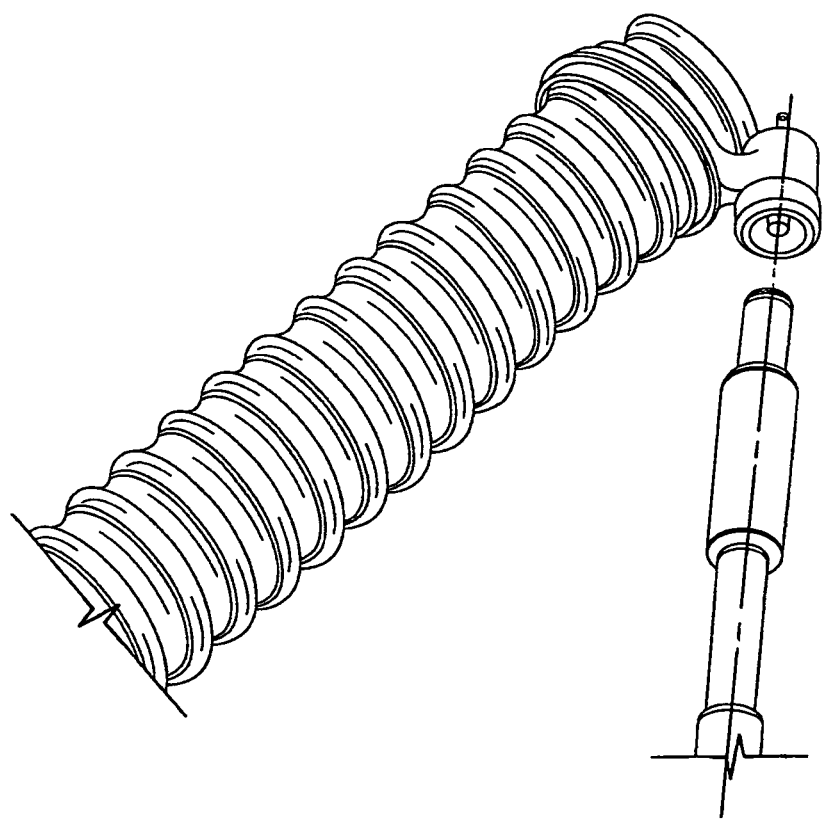
FIG. 20 is a reverse perspective view of the joined support ring and coaxial electrical jack of FIG. 19, and also showing the coaxial power connector of the power supply shown proximate to the corresponding jack.
Figure 21A:
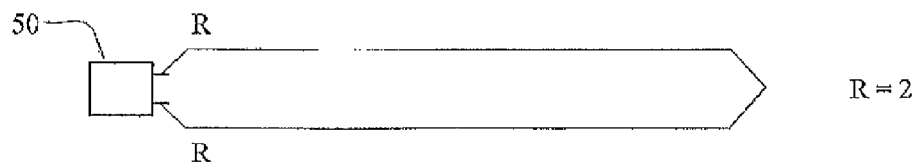
FIGS. 21A-21D schematically illustrate some of the various wire arrangements usable to form the helix of the heated wire hose of the present invention.
Figure 21B:
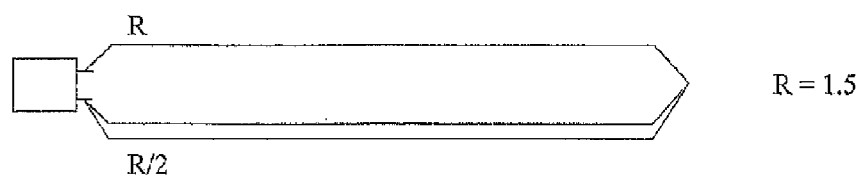
Figure 21C:
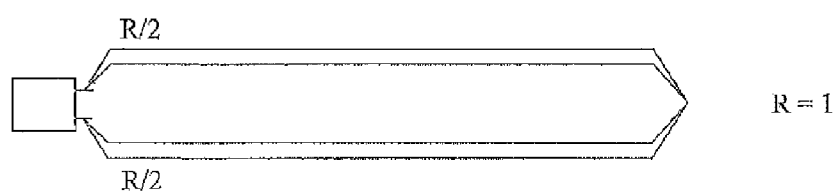
Figure 21D:
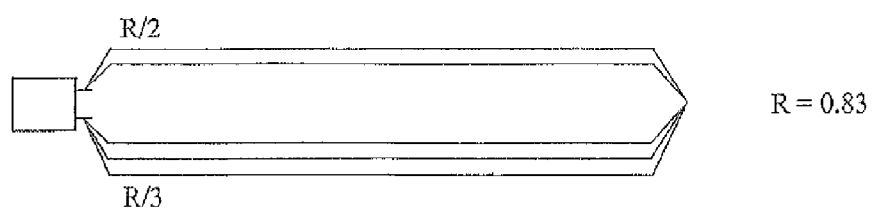

The inner cylindrical surface 33I of cylindrical member 33 of support ring 30 may comprise one or more internal threads that may be used to threadably secure the support ring to the second end of hose 10 (FIG. 2A) or the second end of hose 10N (FIG. 2B), as seen within FIGS. 18-19. This method of engagement allows the position of the support ring 30 on the hose to be the same every time. Although it is possible to utilize less engagement, having at least one full thread to engage at least one turn of the helical reinforcing member may serve to increase the integrity of the connection. Therefore, the threads on the inner cylindrical surface 33I of cylindrical member 33 may have a pitch that may be equal to the pitch of the wire reinforcing member 10W, when being in an undeflected condition. Alternatively, a slightly smaller pitch may be used so that the helical wire reinforcing member 10W may need to be compressed slightly when threadably engaged with the internal threads of inner cylindrical surface 33I of cylindrical member 33, to have more engagement therebetween without having to unnecessarily increase the width of the cylindrical member 33 between first generally planar end 31 and second generally planar end 32.

Instead of having internal threads on inner cylindrical surface 33I of cylindrical member 33 for the connection with the wire reinforcing member 10W, an adhesive may be used to join the support ring 30 with the covered reinforcing member 10W. Also, the adhesive may furthermore be used in addition to where a threadable connection is made between the cylindrical member 33 and the wire reinforcing member 10W, to further improve the integrity of the joint.

Figure 12:
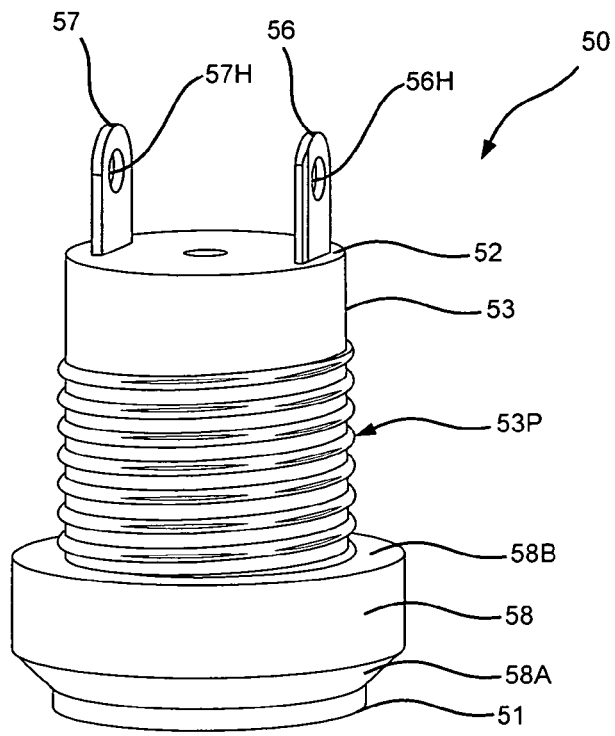
FIG. 12 is a side view of the coaxial electrical jack usable within the receptacle of the support ring, at the first end of the heated hose of FIG. 5.
Figure 13:
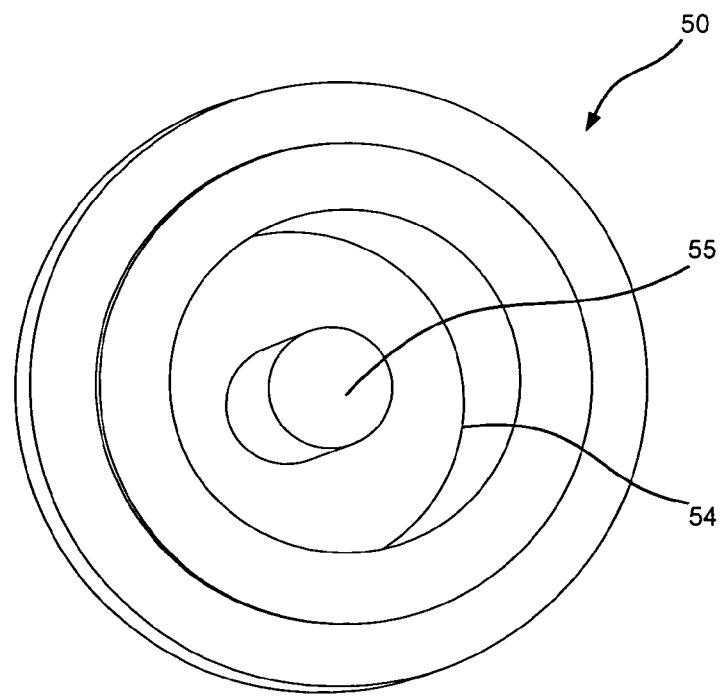
FIG. 13 is an end view of the coaxial electrical jack of FIG. 10.
Figure 14:
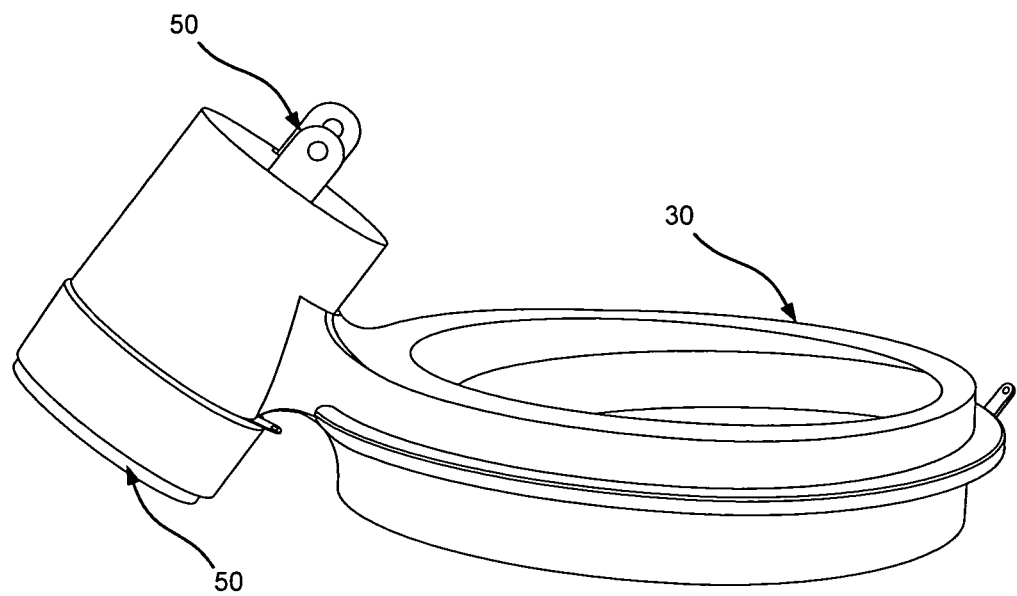
FIG. 14 is a side view of the support ring after having the coaxial electrical jack secured within the receptacle therein.
Figure 15:
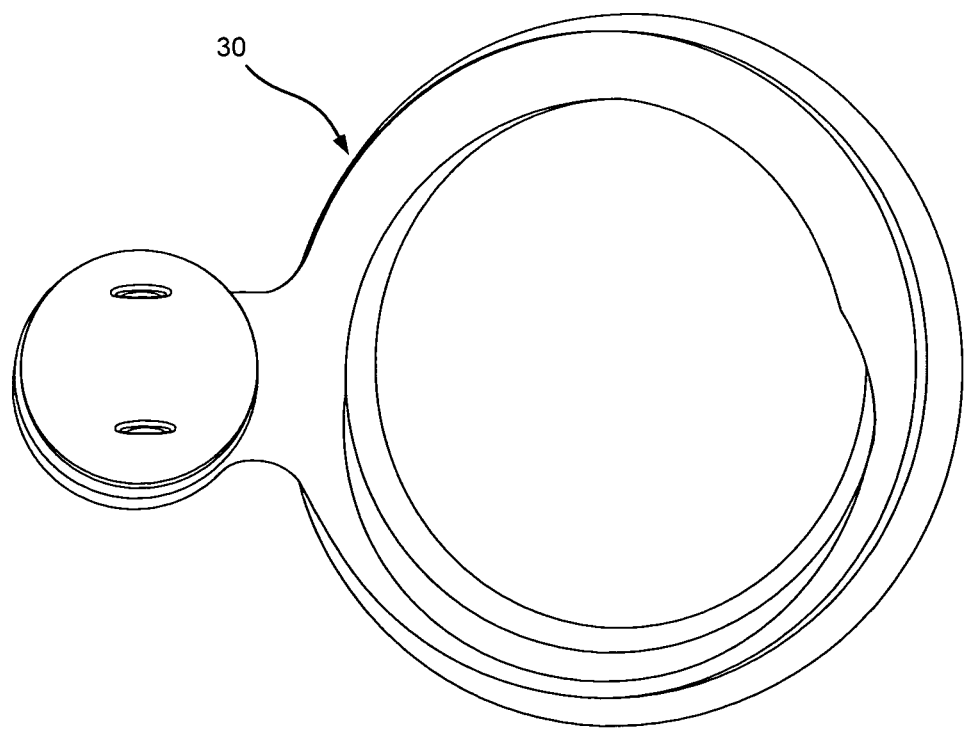
FIG. 15 is a top view of the joined support ring and coaxial electrical jack of FIG. 14.
Figure 16:
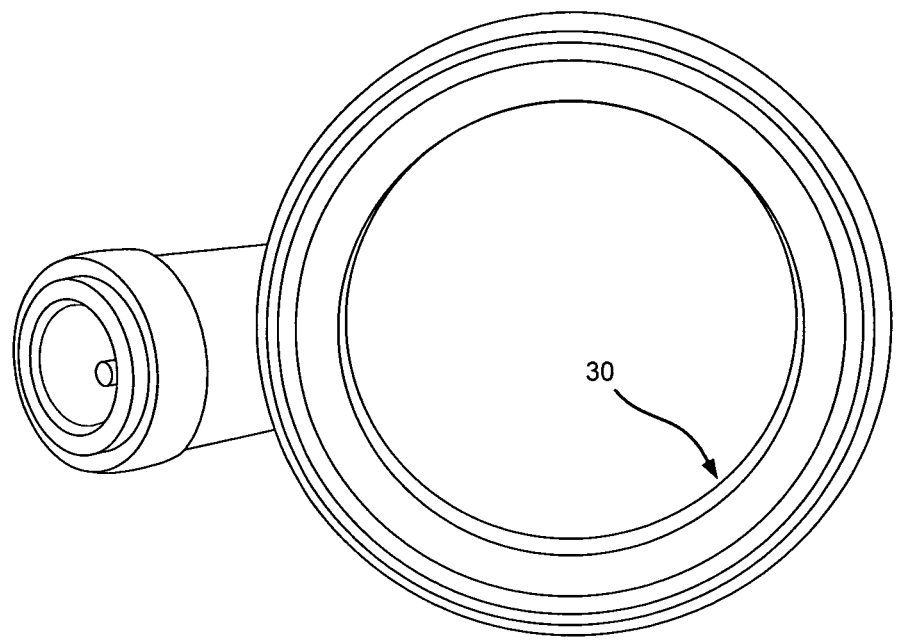
FIG. 16 is a bottom view of the joined support ring and coaxial electrical jack of FIG. 14.
Figure 17:
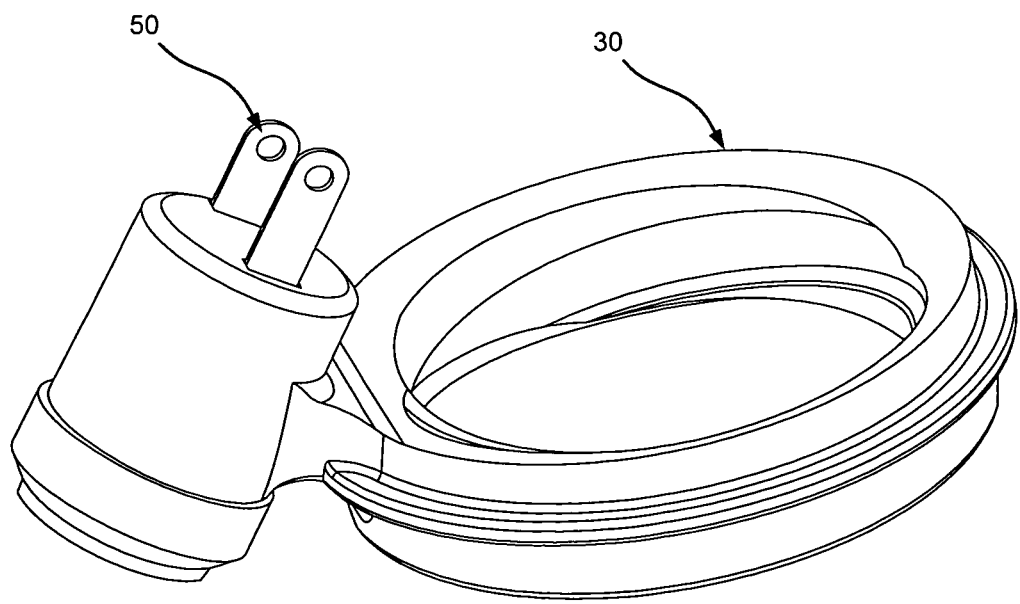
FIG. 17 is a perspective view of the joined support ring and coaxial electrical jack of FIG. 14.

The receptacle 40 of support ring 30, as seen in FIGS. 15-17, may receive an electrical jack 50, which may be the jack shown within FIGS. 12 and 13. Jack 50 may comprise a male) coaxial power connector. Jack 50 may comprise a cylindrical casing 53 that spans between a first end 51 and a second end 52. Extending inward into the cylindrical casing 53 from the first end 51 may be an interior cylindrical metallic contact 54 that may be electrically coupled to a first prong 56 that protrudes from the second end 52 of casing 53. Extending into the interior cylindrical metallic contact 54 from the second end 52, but being electrically insulated therefrom, may be a pin or post 55 that creates the coaxial connector. The post 55 may be electrically coupled to a second prong 57 that protrudes from the second end 52 of casing 53. Protruding outward from the cylindrical casing 53 may be an annular protrusion 58 that spans from a first generally planar end 58A to a second generally planar end 58B, which may be usable for supporting the plastic of the fitting, as discussed hereinafter. The electrical jack 50 may therefore be adapted to be mated with the female power connector 83 of the power supply apparatus 80 shown in FIG. 3, which may further comprise a power supply/converter 81, and a switch 82.

The receptacle 40, as seen in FIG. 19, may receive electrical jack 50 in a friction fit, or in a clearance fit whereby it may be retained therein using adhesive or through the attachment of the wire reinforcing member 10W. In addition, the casing 53 of electrical jack 50 may comprise a series of annular protrusions 53P that may be used to more effectively provide for the interference fit with the inner cylindrical surface 40I of the receptacle 40, with adhesive being applied thereon to provide for a more permanent joining of the two parts.

To be capable of heating the hose in accordance with the current invention, the wire reinforcing member 10W may comprise an energizable heating element that is electrically coupled to the first and second prongs of the jack 50, and may receive current therefrom, which results in the heating of the hose. In a preferred embodiment, the energizable heating element may comprise magnet wire that is commonly used in the construction of transformers and motor windings. The wire may be a copper wire coated with a thin layer of insulation, which may be a first, very thin layer of polyester to serve as primary insulation, and a second layer of nylon serving as secondary insulation. The power supplied, the wire sizes utilized, and the pitch of the windings may preferably be coordinated so as to supply a sufficient amount of heat to suitably warm the hose wall according to the governing specs and to thereby prevent condensation in the hose from forming, by keeping the temperature of the hose wall above the dew point of the moisture laden air being transported therein. The size of the wire may be in the range between 26 AWG to 36 AWG. In one embodiment, for the requisite and efficient heating of typical CPAP hose lengths/diameters, two separate wires, as seen in FIGS. 18-19, may preferably be wound in one direction for the reinforcing member 10W, and may preferably be 29 AWG, 29½ AWG, or 30 AWG. The two adjacent wires, 10W$_A$ and 10W$_B$, being of the same size, have half the resistance of a single wire, and work together to provide more heat than if only a single wire had been used. The double wires, 10W$_A$ and 10W$_B$ may each be secured to the hole 56H in prong 56 of the electrical jack 50 at the second end of the hose, and, after forming the series of helical turns, may be joined to the single wire 10W$_C$ (also forming the helical turns) at the first end of the hose, with the single wire 10W$_C$ being connected to the hole 57H in prong 57 of the electrical jack 50 at the second end of the hose. It should be noted that the electrical jack 50 need not have first and second prongs with holes therein for securing thereto of the double parallel wires 10W$_A$/10W$_B$ and the single wire 10W$_C$. The double parallel wires 10W$_A$/10W$_B$ and the single wire 10W$_C$ may alternatively be directly coupled to the interior cylindrical metallic contact 54 and the pin 55 of the jack, respectively. It should also be noted that other combinations of wire arrangements (instead of the 1+2 arrangement or a 1+1 arrangement) may also be used to selectively dial in the resistance needed to achieve a desired temperature, with increasing numbers of wires potentially being used (2+2, 2+3, 3+3, etc), as long as they may be suitably incorporated into the helix and provide the flexibility desired (see schematics shown in FIGS. 21A-21D).

To be usable with the outlet vent of a CPAP humidifier, the second end of hose 10, as seen in FIG. 19, with the wires soldered or otherwise electrically coupled to the posts of the jack 50, may have plastic adhered thereon to form an integral fitting having a soft resilient cuff for insertion into the CPAP humidifier outlet vent and that also serves to cover and insulate the internal electrical terminations. The plastic 70 may also encapsulate the annular protrusion 34 of cylindrical member 33, as well as the annular protrusion 46 of cylindrical receptacle 40 (see FIG. 5), to thereby further form an integral end fitting with the hose 10W and the support ring 30.

The plastic may be adhered to the hose, the support ring, and the coaxial electrical jack using one of several different approaches. The plastic may be directly molded over selective features of both the support ring and the jack and the hose to integrate them within a single fitting. Alternatively, the plastic may be adhered to the first end of the hose by the plastic cuff being molded separately and thereafter being applied onto the first end of the hose, with the plastic cuff being adhered thereto using either or both adhesive and/or mechanical fasteners, including, but not limited to, a bolt and a nut being used to secure a seam in the soft plastic. Just as with the standard over-molded soft cuff 15 at the first end of the hose, the plastic 70 forming the second end fitting may preferably be formed using the same material as was used for forming the hose, for compatibility—in order for it to bond with the hose portion during an over-molding process, and may preferably be TPE.

Figure 4A:
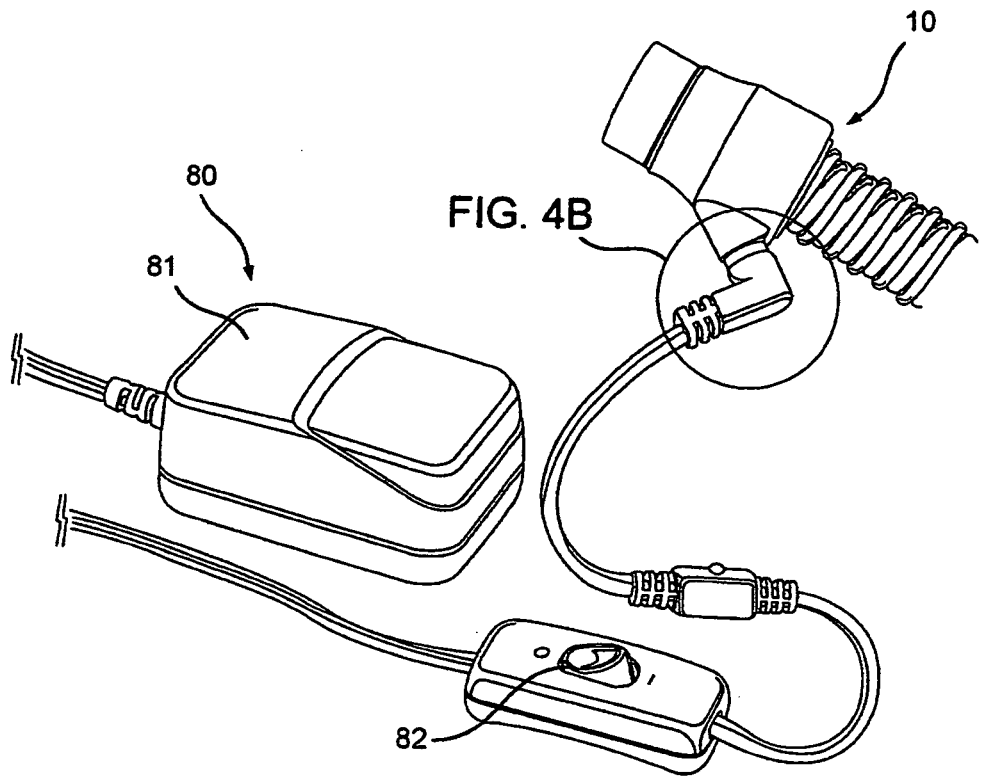
FIG. 4A is the perspective view of the power supply components of FIG. 3, with the coaxial power connector of the power supply shown mated with to the corresponding jack of the heated hose of FIG. 2A.
Figure 4B:
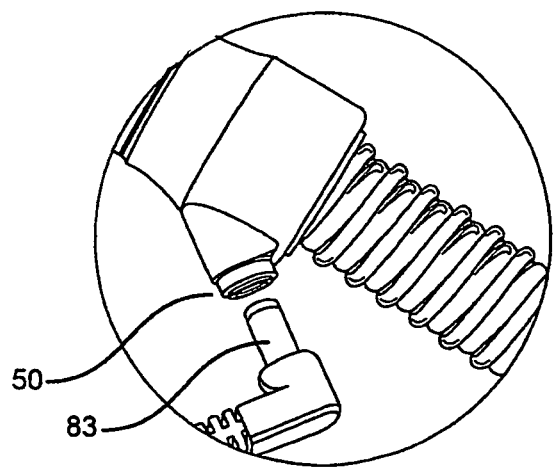
FIG. 4B is an enlarged detail view of the coaxial power connector of the power supply shown disconnected from the corresponding jack of the heated hose.
Figure 5:
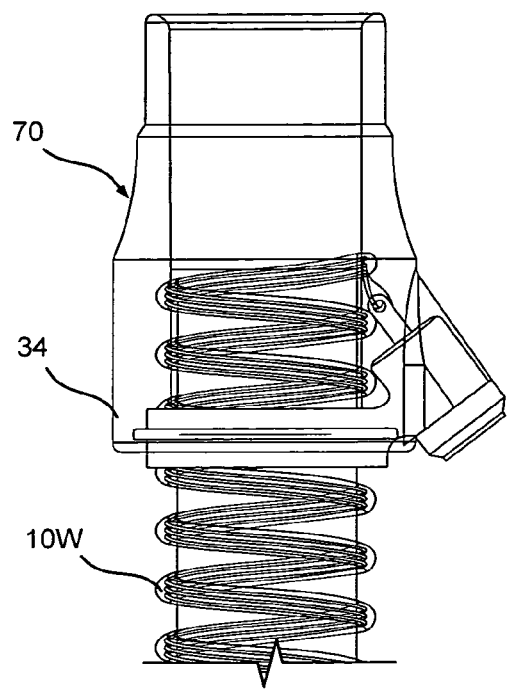
FIG. 5 is a side view of a first end of the heated hose of the current invention, with the coaxial electrical jack and support ring secured thereon, having been over-molded with a soft resilient cuff.
Figure 6:
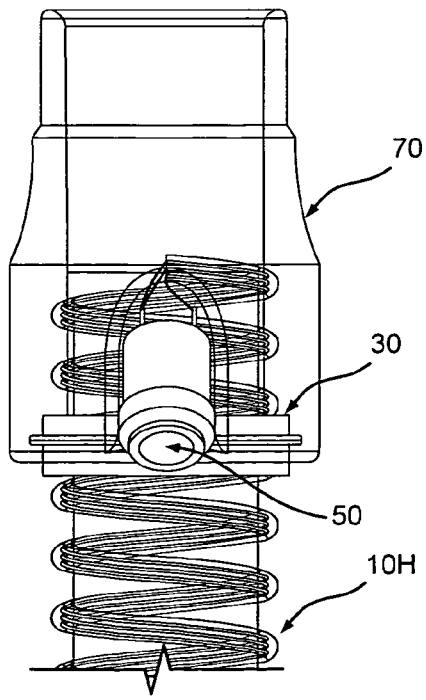
FIG. 6 is a front view of the first end of the heated hose of FIG. 5.
Figure 7:
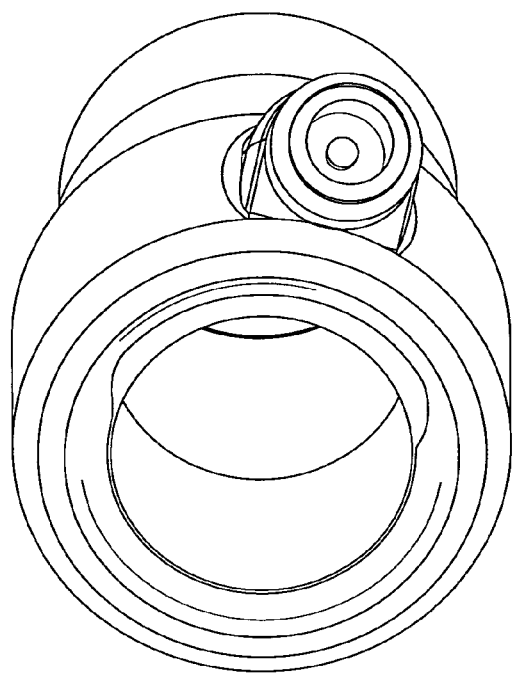
FIG. 7 is an end view of the first end of the heated hose of FIG. 5.
Figure 8:
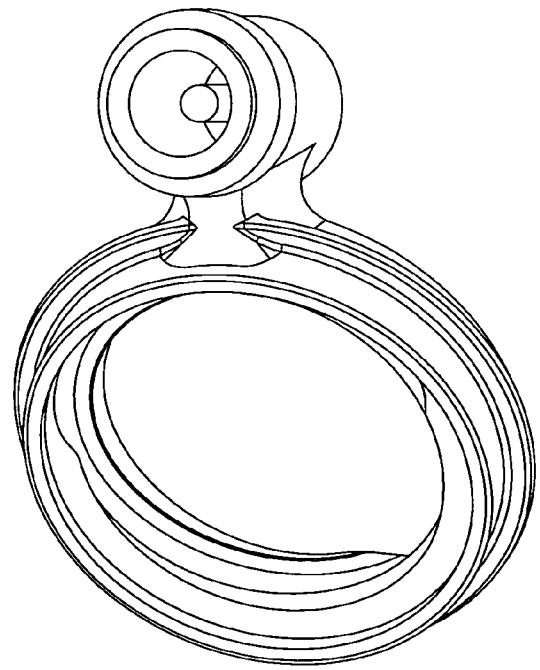
FIG. 8 is an auxiliary view of the heated hose of FIG. 5 showing the interior of the coaxial electrical jack of the first end of the heated hose of FIG. 5.

As noted initially, FIG. 1 shows the second end fitting 20 just prior to being coupled with an outlet vent of a CPAP humidifier 102, and with the coaxial power connector 83 of the power supply shown after being received within the over-molded electrical jack of the heated hose. FIGS. 4A and 4B illustrate connecting and disconnecting of the coaxial power connector 83 with the jack. The hose's independent power supply apparatus 80, shown in FIG. 3, may comprise a switch 82 being electrically coupled to an adapter box 81. The adapter box 81 has plug blades on the far side (not shown), allowing it to be plugged directly into the standard electrical wall socket. The adapter box 81 is constructed to accept different blade sets depending on what country the hose and CPAP machine is to be used. The adapter box 81 is therefore capable of converting whatever power is available, to supply a constant 12 VDC output to the wires of the heated hose.

The examples and descriptions provided merely illustrate a preferred embodiment of the present invention. Those skilled in the art and having the benefit of the present disclosure will appreciate that further embodiments may be implemented with various changes within the scope of the present invention. Other modifications, substitutions, omissions and changes may be made in the design, size, materials used or proportions, operating conditions, assembly sequence, or arrangement or positioning of elements and members of the preferred embodiment without departing from the spirit of this invention.

I claim:

1. A flexible heated wire hose, for use in warming of a wall of the hose to keep its temperature above a dew point of air transported between a CPAP humidifier and a mask to prevent condensation from forming therein, said flexible heated wire hose comprising:
   a hose, said hose having a first end and a second end, said hose comprising a reinforcement member being formed generally into a series of flexible turns with each turn being spaced from an adjacent one of said turns to create an interstitial area; said reinforcement member comprising an electrically energizable heating element; said hose comprising one or more layers of a flexible material, said one or more flexible layers of material being formed to overlay at least a portion of said series of turns of said reinforcement member and corresponding interstitial area between said turns; and
   a first end fitting, said first end fitting for use in attaching said hose to the CPAP humidifier, said first end fitting comprising:
      a support ring, said support ring comprising: a hollow cylindrical member, and a receptacle joined to said cylindrical member; an inside surface of said hollow cylindrical member comprising one or more internal threads configured to threadably engage a corresponding one or more of said series of turns of said reinforcement member, proximate to a first end of said hose, to threadably secure said support ring to said hose; a first end of said receptacle comprising an opening into a cavity therein, said joining of said receptacle to said cylindrical member configured for said opening at said first end of said receptacle to face in a substantially opposite direction with respect to an opening of said hose at said first end of said hose, a second end of said receptacle comprising a first opening and a second opening each configured to interconnect with said cavity;
      an electrical jack, said electrical jack comprising an electrical connector at a first end of said jack, and a first prong and a second prong at a second end of said jack, said electrical jack configured to be received into said receptacle cavity through said first opening at said first end of said receptacle, with said first prong and said second prong configured to respectively protrude out from said first and second openings at said second end of said receptacle, and with said connector configured to be exposed at said opening of said first end of said receptacle, said energizable heating element being electrically coupled to said first and second prongs of said electrical jack;

over-molded plastic, said over-molded plastic configured to encapsulate: said support ring, said electrical coupling of said heating element with said electrical jack, and said receptacle, except for said exposed connector of said electrical jack; said over-molded plastic configured to extend beyond said reinforcement member at said first end of said hose, and to neck down thereat to form a soft cuff with an opening therein; and wherein said opening in said soft cuff is configured be open in said substantially opposite direction with respect to an opening of said connector, said connector thereby configured to receive a mating connector of a power supply in an umbilical arrangement; wherein said internal threads of said cylindrical member of said support ring comprise a pitch being less than a pitch of said turns of said reinforcing member when in an undeflected condition, thereby requiring compression of said corresponding one or more of said series of turns of said reinforcement member for said threaded engagement therewith.

2. The heated wire hose according to claim 1 further comprising a second end fitting at said second end of said hose, said second end fitting comprising over-molded plastic formed into a soft cuff.

3. The heated wire hose according to claim 1 wherein said support ring secured to said one or more of said series of turns of said reinforcement member further comprises an adhesive between said internal threading on said inside surface of said cylindrical member and said hose.

4. The heated wire hose according to claim 3 wherein said electrical jack comprises a coaxial electrical jack.

5. The heated wire hose according to claim 4 wherein said electrically energizable heating element comprises:
a first wire and a second wire being electrically coupled to said first prong of said jack at said first end of said hose;
a third wire being insulated from said first and second wires and being electrically coupled to said second prong of said jack at said first end of said hose;
wherein said first and second wires and said third wire are each formed into said series of flexible turns; and
wherein said first and second wires are electrically coupled to said third wire at said second end of said hose.

6. The heated wire hose according to claim 1 wherein said joining of said receptacle to said cylindrical member for said opening of said receptacle to face in said substantially opposite direction with respect to said opening of said hose first end comprises an axis of said receptacle configured to be at a 45 degree angle to an axis of said cylindrical member.

7. The heated wire hose according to claim 1 wherein said joining of said receptacle to said cylindrical member comprises said receptacle being integrally formed with said cylindrical member.

8. The heated wire hose according to claim 1 wherein said flexible material comprises a thermoplastic elastomer.

9. The heated wire hose according to claim 5 further comprising a second end fitting at said second end of said hose, said second end fitting comprising over-molded plastic formed into a soft cuff.

10. A flexible heated wire hose comprising:
a hose, said hose having a first end and a second end, said hose comprising a reinforcement member formed generally into a series of flexible turns with each turn being spaced from an adjacent one of said turns to create an interstitial area; said reinforcement member comprising an electrically energizable heating element; said hose comprising one or more layers of a flexible material formed to overlay at least a portion of said series of turns of said reinforcement member and corresponding interstitial area; and
a first end fitting, said first end fitting comprising:
an electrical jack;
a support ring, said support ring comprising a hollow cylindrical member, and a receptacle joined to said cylindrical member, an inside surface of said hollow cylindrical member comprising one or more internal threads configured to threadably engage a corresponding one or more of said series of turns of said reinforcement member, proximate to a first end of said hose; said receptacle of said support ring configured to receive said electrical jack in a cavity therein, with a connector at a first end of said jack configured to be exposed therefrom and to face in in a substantially different direction with respect to an opening of said hose at said first end of said hose; said energizable heating element being electrically coupled to said connector of said electrical jack; and
over-molded plastic configured to encapsulate said support ring, said electrical coupling of said heating element with said electrical jack, and said electrical jack, except for said connector; said over-molded plastic configured to extend beyond said first end of said hose to form a soft cuff with an opening into said hose; and
wherein said opening in said soft cuff is configured be open in said substantially opposite direction with respect to an opening of said connector; wherein said internal threads of said cylindrical member of said support ring comprise a pitch being less than a pitch of said turns of said reinforcing member when in an undeflected condition, thereby requiring compression of said corresponding one or more of said series of turns of said reinforcement member for said threaded engagement therewith.

11. The heated wire hose according to claim 10 wherein said support ring secured to said one or more of said series of turns of said reinforcement member further comprises an adhesive between said internal threading on said inside surface of said cylindrical member and said hose.

12. The heated wire hose according to claim 11 wherein said electrical jack comprises a coaxial electrical jack, said coaxial electrical jack comprising first and second electrical prongs coupled to first and second contacts of said jack, said first and second prongs configured to extend from a second end of said jack, and to protrude out from corresponding openings in said receptacle; and wherein said energizable heating element is electrically coupled to said first and second prongs.

13. The heated wire hose according to claim 12 wherein said electrically energizable heating element comprises:
a first wire and a second wire being electrically coupled to said first prong of said jack at said first end of said hose;
a third wire being insulated from said first and second wires and being electrically coupled to said second prong of said jack at said first end of said hose;
wherein said first and second wires and said third wire are each formed into said series of flexible turns; and wherein said first and second wires are electrically coupled to said third wire at said second end of said hose.

14. The heated wire hose according to claim 13 wherein an axis of said connector of said electrical jack is at a 45 degree angle to an axis of said soft cuff of said first end fitting.

15. The heated wire hose according to claim 14 wherein said flexible material comprises a thermoplastic elastomer.

16. The heated wire hose according to claim 15 further comprising a second end fitting at said second end of said hose, said second end fitting comprising plastic over-molded over said second end of said hose to form a soft cuff.

17. A flexible heated wire hose comprising:
- a reinforcement member formed into a series of flexible turns, having a first end and a second end, each of said turns spaced from an adjacent one of said turns to create an interstitial area, said reinforcement member comprising an electrically energizable heating element;
- one or more layers of a flexible material formed to overlay at least a portion of said series of turns of said reinforcement member and corresponding interstitial area, to create an opening and each of said first and second ends; and
- an end fitting comprising:
  - an electrical jack;
  - a receptacle;
  - a hollow support ring, said receptacle joined to an outside surface of said support ring, an inside surface of said hollow support ring comprising one or more internal threads configured to threadably engage a corresponding one or more of said series of turns of said reinforcement member, proximate to its first end; said receptacle configured to receive said electrical jack therein, with a connector at a first end of said jack configured to be exposed therefrom and to face in in a substantially different direction with respect to said opening at said first end; said energizable heating element being electrically coupled to said connector; and
  - over-molded plastic configured to encapsulate said support ring, said electrical coupling of said heating element with said electrical jack, and said electrical jack, except for said connector; said over-molded plastic configured to extend beyond said first end to form a soft cuff; wherein said internal threads of said cylindrical member of said support ring comprise a pitch being less than a pitch of said turns of said reinforcing member when in an undeflected condition, thereby requiring compression of said corresponding one or more of said series of turns of said reinforcement member for said threaded engagement therewith.

* * * * *